United States Patent
Kulkarni et al.

(10) Patent No.: US 8,970,840 B2
(45) Date of Patent: Mar. 3, 2015

(54) METHOD AND APPARATUS FOR AEROSOL ANALYSIS USING OPTICAL SPECTROSCOPY

(75) Inventors: Pramod Kulkarni, Mason, OH (US); Prasoon Diwakar, Cincinnati, OH (US)

(73) Assignee: The United States of America, as Represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 713 days.

(21) Appl. No.: 13/315,372

(22) Filed: Dec. 9, 2011

(65) Prior Publication Data

US 2013/0148117 A1  Jun. 13, 2013

(51) Int. Cl.
| | |
|---|---|
| *G01J 3/30* | (2006.01) |
| *G01N 21/67* | (2006.01) |
| *G01N 15/06* | (2006.01) |
| *G01N 1/22* | (2006.01) |

(52) U.S. Cl.
CPC ............. *G01N 21/67* (2013.01); *G01N 15/06* (2013.01); *G01N 2001/2223* (2013.01)
USPC ........................................................ 356/313

(58) Field of Classification Search
CPC .............. G01N 2001/2223; G01N 15/0606; G01N 21/67
See application file for complete search history.

(56) References Cited

U.S. PATENT DOCUMENTS

| | | | |
|---|---|---|---|
| 3,653,766 A | 4/1972 | Walters et al. | |
| 3,736,059 A | 5/1973 | Schuhknecht et al. | |
| 4,769,609 A * | 9/1988 | Masuda | 324/455 |
| 4,968,885 A * | 11/1990 | Willoughby | 250/288 |
| 5,153,519 A | 10/1992 | Wentworth et al. | |
| 5,455,417 A * | 10/1995 | Sacristan | 250/287 |
| 7,530,265 B2 | 5/2009 | DiFoggio | |
| 7,605,910 B2 * | 10/2009 | Ahn | 356/37 |
| 7,701,578 B1 * | 4/2010 | Herring | 356/417 |
| 7,852,469 B1 * | 12/2010 | Sickenberger et al. | 356/256 |
| 7,862,649 B2 | 1/2011 | Sakuma et al. | |
| 8,007,566 B2 | 8/2011 | Abdelkrim et al. | |
| 2007/0234901 A1 * | 10/2007 | Pletcher et al. | 95/78 |
| 2011/0316552 A1 * | 12/2011 | Shinada et al. | 324/464 |

FOREIGN PATENT DOCUMENTS

| | | |
|---|---|---|
| WO | WO-2010/003613 A1 | 1/2010 |
| WO | 2012/048308 A2 | 4/2012 |

OTHER PUBLICATIONS

Prasoon Diwakar, Pramod Kulkarni & M. Eileen Birch, "New Approach for Near-Real-Time Measurement of Elemental Composition of Aerosol Using Laser-Induced Breakdown Spectroscopy", *Aerosol Science and Technology*, 46:3, 316-332 (2012).

(Continued)

*Primary Examiner* — Kara E Geisel
*Assistant Examiner* — Maurice Smith
(74) *Attorney, Agent, or Firm* — Gifford, Krass, Sprinkle, Anderson & Citkowski, P.C.; Douglas L. Wathen

(57) ABSTRACT

Particles of a flow of aerosol are collected and analyzed by passing them through a housing having an inlet area, an outlet area, and a collection and analysis area interconnecting the inlet and outlet areas. A collection electrode has a tip disposed in the collection and analysis area and particles are collected thereon. After collection, the particles are ablated and atomic emissions are collected for analysis of the particles.

23 Claims, 7 Drawing Sheets

(56) References Cited

OTHER PUBLICATIONS

Prasoon Diwakar, Pramod Kulkarni, Eileen Birch, "Semi-Continuous Measurement of Elemental Composition of Aerosol Particles Using Laser Induced Breakdown Spectroscopy," AAAR 29th Annual Conference, presented by the American Association for Aerosol Research, Abstract only (2010).

* cited by examiner

METHOD AND APPARATUS FOR AEROSOL ANALYSIS USING OPTICAL SPECTROSCOPY

GOVERNMENT INTEREST

The invention described herein may be manufactured, used, and licensed by or for the United States Government.

FIELD OF THE INVENTION

The present invention relates generally to methods and apparatus for the collection and analysis of particles of a flow of aerosol.

BACKGROUND OF THE INVENTION

An aerosol is a suspension of fine solid particles or liquid droplets in a gas. There is a need to collect and analyze the particles of an aerosol especially where the particles of aerosol are unidentified or include pollutants that must be monitored or limited. There have been numerous attempts to provide instruments far the collection and analysis of particles of an aerosol. However, each of these approaches has had certain drawbacks. As such, there is a need for improved real-time or semi-continuous methods and apparatus for the collection and analysis of particles of an aerosol.

SUMMARY OF THE INVENTION

The present invention provides methods and apparatus for the collection and analysis of particles of an aerosol. In a first embodiment of such a method, a housing is provided having an inlet area and an outlet area. The housing further has a collection and analysis area interconnecting the inlet area with the outlet area. A flow path for an aerosol is defined from the inlet area, through the outlet and collection area, and out the outlet area. A collection electrode is provided having a tip disposed in the flow path in the collection and analysis area. A flow of aerosol is introduced along the flow path and particles of the aerosol are collected on the tip of the collection electrode. A second electrode is provided spaced from the collection electrode tip so as to define a spark gap in the collection and analysis area. A high voltage pulse generator is provided connected to the collection electrode and second electrode for generation of a spark across the spark gap. A high voltage spark is applied across the spark gap so as to ablate the particles collected on the tip of the collection electrode thereby creating atomic emissions. An optical window is provided in the housing, with the window being aligned with the spark gap. Atomic emissions are collected for analysis.

In some versions of this method, the particles of the aerosol passing along the flow path are charged and during the collection step the collection electrode is held at a bias voltage relative to the charged particles such that the charged particles collect on the tip of the collection electrode. During this collection step, a corona may be produced by the second electrode such that the second electrode creates a cloud of ions and the particles of the aerosol are charged by the ions from the second electrode. Alternatively, during the collection step, the second electrode may be held at a voltage sufficient to create an electrical field so as to urge the charged aerosol particles towards the tip of the collection electrode.

In some versions, a collection electrode assembly is provided, with the collection electrode being a central electrode of the collection electrode assembly. The assembly further includes at least one concentric electrode surrounding the central electrode and a dielectric layer separating the central electrode from the concentric electrode. The concentric electrode is held at a potential greater than the central electrode when the central collection electrode is held at the bias voltage relative to the charged particles.

In some embodiments, the collection electrode and second electrode are each elongated and are coaxial with one another. The housing may also be elongated, with the electrodes extending coaxially along the housing and the window being disposed in a side wall of the housing.

In some embodiments, the inlet area of the housing has a first surface and a second surface spaced therefrom. The first and second surfaces are each formed of an electrically conductive material. An aerosol inlet is defined adjacent to the first surface and a sheath flow inlet is defined between the aerosol inlet and the second surface of the inlet area. The flow path for the aerosol is defined from the aerosol inlet of the inlet area, through the collection and analysis area, and out the outlet area. A sheath flow (free of any particles) path is defined from the sheath inlet of the inlet area, through the collection and analysis area, and out the outlet area. During the collection step, the first surface of the inlet area is grounded relative to the charged particles, a sheath flow is introduced along the sheath flow path, and the second surface is held at a classification voltage chosen such that a portion of the charged particles are deflected toward the second surface and towards the collection electrode tip. In some versions, the housing is an elongated tube defining at least the inlet area and the collection and analysis area, with the first surface of the inlet area being defined by the inner surface of the tube. A central member is provided which extends axially along the inlet area of the housing to a downstream end, with the central member having an outer surface defining the second surface of the inlet area. A coaxial flow guide may be provided in the inlet area between the central member and the elongated tube, with the coaxial flow guide having a downstream end disposed upstream of the downstream end of the central member. The aerosol flow path extends between the flow guide and the elongated tube and the sheath flow path extends between the flow guide and the central member. The second electrode may have a tip that is adjacent the downstream end of the central member.

In a further embodiment, the housing has a first surface and an opposed second surface, with the first surface formed of an electrically conductive material and the second surface formed of a dielectric material. An aerosol inlet is defined adjacent the first surface in the inlet area, with the aerosol flow path defined from the aerosol inlet of the inlet area, through the collection and analysis area, and out the outlet area. A sheath flow inlet is defined between the aerosol inlet and the second surface, with a sheath flow path being defined from the sheath flow inlet, through the collection and analysis area, and out through the outlet area. The collection electrode comprises a plurality of collection electrodes having tips disposed in or extending from the second surface, with these tips being spaced apart along the second surface of the collection and analysis area. The second electrode comprises a plurality of second electrodes disposed in or extending from the first surface, with these second electrodes being spaced apart along the first surface and registered with the collection electrodes so as to define a plurality of spark gaps. During the collection step, the plurality of collection electrodes are each held at a bias voltage relative to the charged particles, a sheath flow is introduced along the sheath flow path, and the first surface is held at a classification voltage such that a portion of the charged particles are deflected toward the second surface for collection on the tips of the plurality of spaced apart collection electrodes, wherein each electrode tip collects particles of a different charge. During the spark applying step, a high voltage spark is applied across each of the plurality of spark gaps. In some versions, the high voltage spark is applied across each spark gap at a different time. A flow guide may be disposed in the inlet area between the aerosol flow path and the sheath flow path.

In yet a further embodiment, a charger is provided for charging particles of the flow of aerosol and a size classification unit is provided to sort particles of the flow of aerosol into a plurality of sorted aerosol flows. Each of the sorted flows has particles within a predetermined size range. In this embodiment, the collection electrode and the second electrode are part of a plurality of collection electrodes and second electrodes each separated so as to define a spark gap, with each collection electrode tip being disposed in a flow path for one of the sorted flows. The size classification unit may comprise a plurality of cyclone separators.

In some embodiments, the method further comprises providing a broadband optical spectrometer in optical communication with the optical window and analyzing the atomic emissions in the spectrometer. A fiber optic cable may be provided with one end of the fiber optic cable forming or being in optical communication with the optical window and the opposite end of the fiber optical cable being in optical communication with the spectrometer.

In another embodiment, the method further comprises providing a laser light source and using the laser light source to ablate particles on the collection electrode tip prior to applying the high voltage spark.

A spark emission spectroscopy device in accordance with an embodiment of the present invention includes a housing having an inlet area and an outlet area. The housing further has a collection and an analysis area interconnecting the inlet area with the outlet area. A flow path for an aerosol is defined from the inlet area, through the collection and analysis area, and out the outlet area. A collection electrode has a tip disposed in the collection and analysis area and in the flow path for collection of particles of an aerosol thereon. A second electrode is spaced from the collection electrode tip so as to define a spark gap in the collection and analysis area. An optical window is defined in the housing, with the window being aligned with the spark gap. A high voltage pulse generator is connected to the collection electrode and second electrode for generation of a spark across the spark gap. The collection electrode is held at a bias voltage during the collection step, whereby charged particles of a flow of aerosol passing along the flow path are collected on the collection electrode tip. During a spark ablation step, a high voltage pulse is applied between the second electrode and collection electrode tip so as to create a spark across the spark gap, thereby ablating aerosol particles collected on the tip of the collection electrode.

According to a further embodiment of the present invention, a method is provided for collecting and analyzing particles of a flow of aerosol. A housing is provided having an inlet area and an outlet area. The housing further has a collection and analysis area interconnecting the inlet area with the outlet area. The inlet area of the housing has a first surface and a second surface spaced therefrom. An aerosol inlet is defined adjacent the first surface and a sheath flow inlet is defined between the aerosol inlet and the second surface of the inlet area. A flow path for an aerosol is defined from the aerosol inlet of the inlet area, through the collection and analysis area, and out the outlet area. A sheath flow path is defined from the sheath inlet of the inlet area, through the collection and analysis area, and out the outlet area. A collection electrode is provided having a tip disposed in the aerosol flow path in the collection and analysis area. During a collection step, the flow of aerosol is introduced along the aerosol flow path, with the particles of the aerosol being charged. A sheath flow is introduced along the sheath flow path. The collection electrode is held at a bias voltage relative to the charged particles. The first or second surface of the inlet area is held at a classification voltage chosen such that a portion of the charged particles are deflected toward the tip of the collection electrode. As such, some of the charged particles deflected toward the tip of the collection electrode are collected on the tip. During an analysis step, particles collected on the tip of the collection electrode are ablated, thereby creating atomic emission, and these atomic emission signals are collected during at least part of the spark step, such as after a short delay from the start of the spark, for analysis of the ablated particles.

In some versions, a second electrode is spaced from the collection electrode tip so as to define a spark gap in the collection and analysis area, a high voltage pulse generator is provided, and a high voltage spark is applied across the spark gap so as to perform the ablating step.

In certain versions, the first and second surfaces are each formed of an electrically conductive material. During the collection step, the first surface of the inlet area is grounded relative to the charged particles and the second surface is the surface that is held at the classification voltage such that a portion of the charged particles are deflected towards the second surface and towards the tip of the collection electrode.

In an alternative embodiment, the first surface of the inlet area is formed of an electrically conductive material and the second surface of the inlet area is formed of a dielectric material. The collection electrode comprises a plurality of collection electrodes each having tips disposed in or extending from the second surface. The tips of the plurality of collection electrodes are spaced apart along the second surface in the collection and analysis area. During a collection step, the plurality of electrodes are each held at a bias voltage relative to the charged particles and the first surface is the surface held at the classification voltage such that a portion of the charged particles are deflected towards the second surface for collection on the tips of the plurality of spaced apart collection electrodes. Each collection electrode tip collects particles of a different charge. During the ablating step, the particles are ablated on the tips of each of the collection electrodes.

DETAILED DESCRIPTION OF THE PREFERRED EMBODIMENTS

The present invention provides both methods and apparatus for the collection and analysis of particles of an aerosol. In preferred embodiments, particles of the aerosol are collected on the tip of a collection electrode and these particles are then ablated so as to create atomic emissions that are collected for analysis of the particles. In preferred embodiments, the particles of the aerosol are charged either as part of the present invention or prior to introduction to the apparatus or method, and the collection electrode is held at a bias voltage, which may be ground, relative to the charged particles such that these charged aerosol particles collect on the tip of the collection electrode. In some preferred embodiments, a second electrode is provided spaced from the collection electrode tip and after particles are collected on the tip a high voltage spark is created between the collection electrode and second electrode so that the spark ablates the particles. In certain embodiments, charged particles of the aerosol are deflected by a surface held at a classification voltage such that particles collected on the tip of the collection electrode are sorted. Multiple collection electrodes may be provided such that each collection electrode collects particles of a different charge and/or size.

Figure 1:
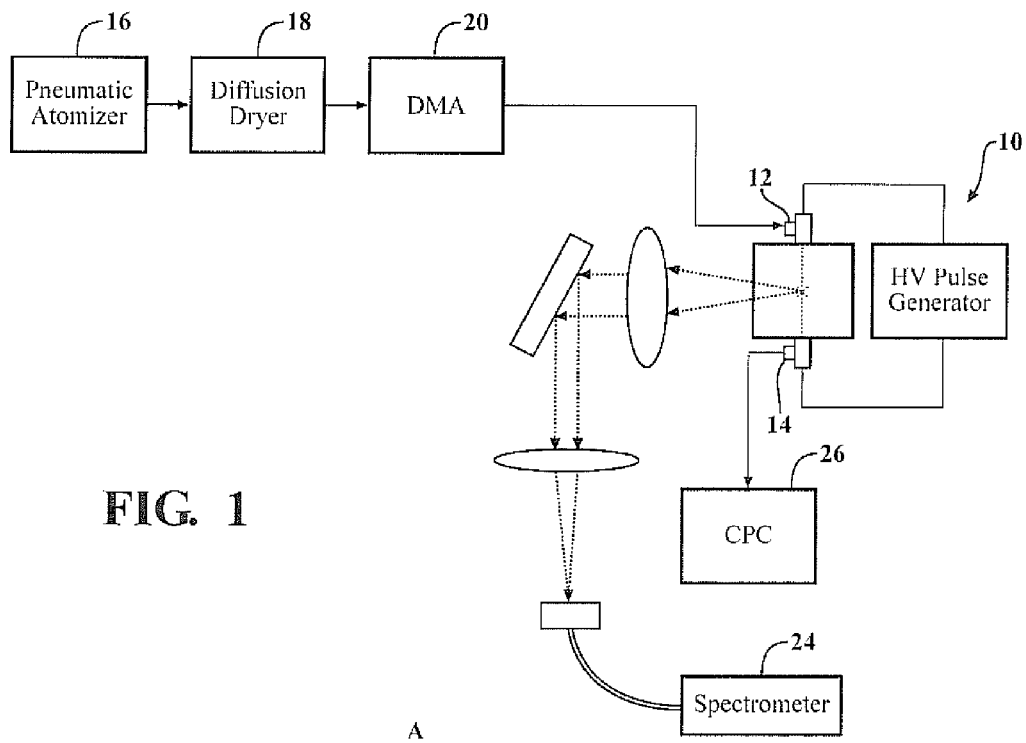
FIG. 1 is a schematic view of a testing setup for an embodiment of the present invention.

Referring to FIG. 1, a test setup for testing an embodiment of the present invention is illustrated schematically. An embodiment of the present invention is shown generally at 10. This embodiment consists of an apparatus for collection and analysis of particles of an aerosol. An aerosol is introduced to the apparatus at inlet 12 and exits through an outlet shown at 14. In this testing configuration, an aerosol is provided to the apparatus 10 using a pneumatic atomizer 16 to create an aerosol and a diffusion dryer 18 to remove excess moisture. The resulting aerosol is passed through a differential mobility analyzer 20 and then introduced to the inlet 12 of the apparatus 10. As will be described in more detail hereinbelow, particles of the aerosol are collected inside the apparatus 10 and then ablated to create atomic emissions 22. These atomic emissions are then collected for analysis, such as by a spectrometer 24. In this test setup, the remaining flow exits outlet 14 and is introduced into a condensation particle counter 26. By using the differential mobility analyzer 20 to analyze the flow prior to introduction to the apparatus 10, and the condensation particle counter 26 to analyze the flow remaining after the apparatus 10, the apparatus may be tested and/or calibrated.

Figure 2:
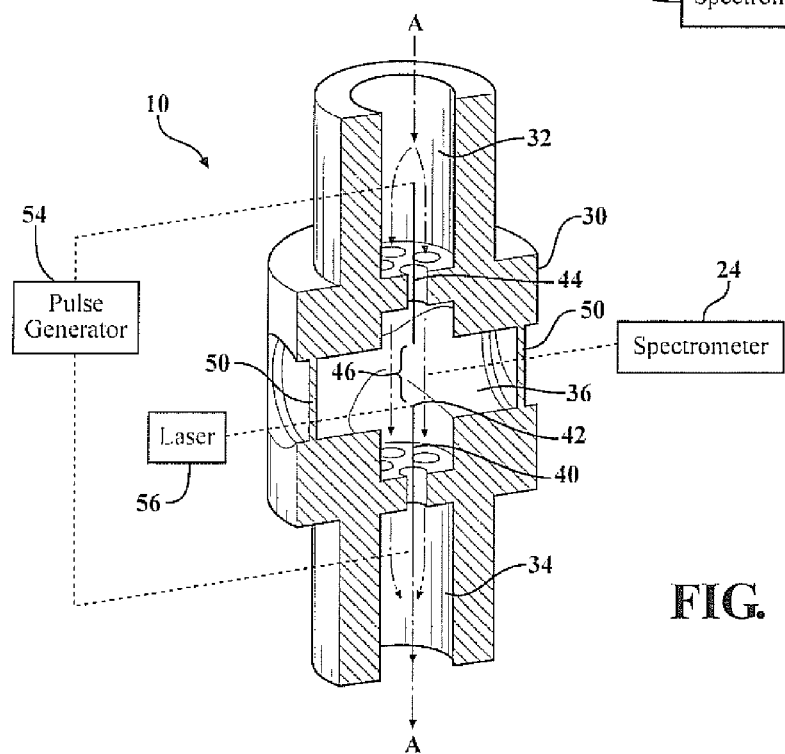
FIG. 2 is a cross sectional perspective view of a portion of an embodiment of the present invention.

FIG. 2 illustrates a cross-sectional view of an apparatus in accordance with an embodiment of the present invention. This apparatus corresponds to the apparatus 10 in FIG. 1. The apparatus 10 includes a housing 30 having an inlet area 32, an outlet area 34, and a collection and analysis area 36 interconnecting the inlet area with the outlet area. An aerosol flow path is generally illustrated at A. This aerosol flow path extends from the inlet area, through the collection and analysis area, and out the outlet area. A collection electrode 40 has a tip 42 that is disposed in the flow path in the collection and analysis area 36. In this embodiment, a second electrode 44 is spaced from the collection electrode tip 42 so as to define a spark gap 46 in the collection and analysis area 36. In this embodiment, the overall housing 30 is generally tubular and elongated and the collection electrode 40 and second electrode 44 are each elongated and coaxial with each other and with the housing. At least one optical window 50 is provided in the housing in alignment with the spark gap 46. By saying that the optical window is in alignment with the spark gap 46 it is meant that the window has an optical view of the spark gap, which may be either direct or indirect, such that atomic emissions from the spark gap may be collected through the optical window 50. In this embodiment, a second optical window 52 is provided on an opposite side of the spark gap. A high voltage pulse generator 54 is connected to the collection electrode 44 and second electrode 40 for generation of a spark across the spark gap 46.

During operation, a flow of aerosol is introduced along path A. In some versions, the particles of the aerosol are charged prior to entering the inlet area 32, such as by passing the flow of aerosol through a unipolar or bipolar charger. During a collection step, the collection electrode 40 is held at a bias voltage relative to the charged particles such that particles collect on the tip of the electrode. The bias voltage may be approximately zero or ground or may be a different voltage for attracting the charged particles. As used herein, "ground" means that an electrode or other component is at ground relative to the high voltage electrode but may not be at an absolute ground. In another version, the flow of aerosol introduced along path A is charged by the second electrode 44. In this version, during a collection step, the second electrode is provided with a corona current so as to hold the second electrode at a corona voltage sufficient to create a cloud of ions around the second electrode. These ions then mix with the particles of the aerosol causing the particles to be charged and thereby attracted to the collection electrode 40. In an alternative version, the second electrode is held at a voltage that creates an electrical field that generally urges the particles towards the collection electrode.

During a subsequent step, particles collected on the tip 42 of the collection electrode 40 are ablated so as to create atomic emissions for analysis of the particles. In some versions, the high voltage pulse generator 54 creates a high voltage spark across the spark gap, thereby ablating the particles. A spectrometer 24 may be in optical communication with the window 50 so as to collect atomic emissions from the ablated particles. Optical communication between the spectrometer 24 and the spark gap may be achieved by a fiber optic cable with one end in optical communication with the window 50, or actually forming the window, and the other end connected to the spectrometer.

In an alternative embodiment, a laser 56 is provided so as to provide a laser light source for ablating particles on the tip 42 of the collection electrode 40. The laser 56 and pulse generator 54 may be used in combination, such as by using the laser to first ablate the particles from the tip 42 and then using the pulse generator 54 to form a plasma to create the atomic emissions.

Figure 3:
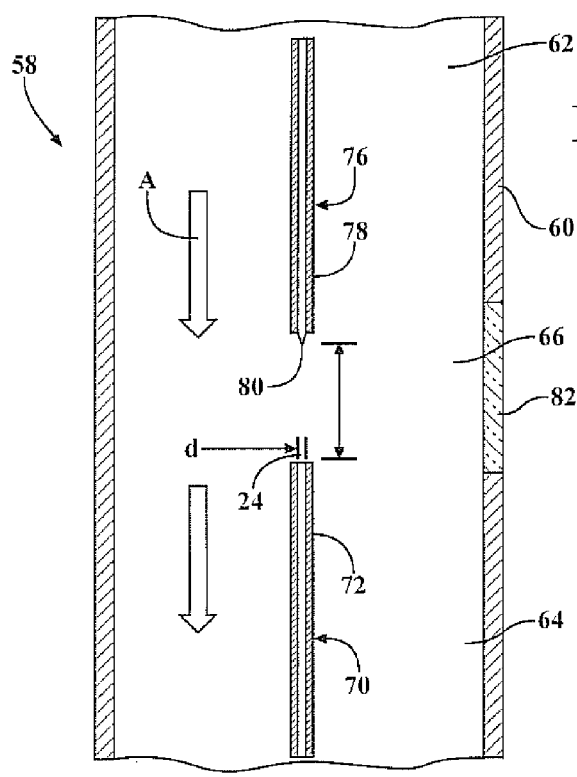
FIG. 3 is a cross sectional view showing part of an embodiment of the present invention.
Figure 4:
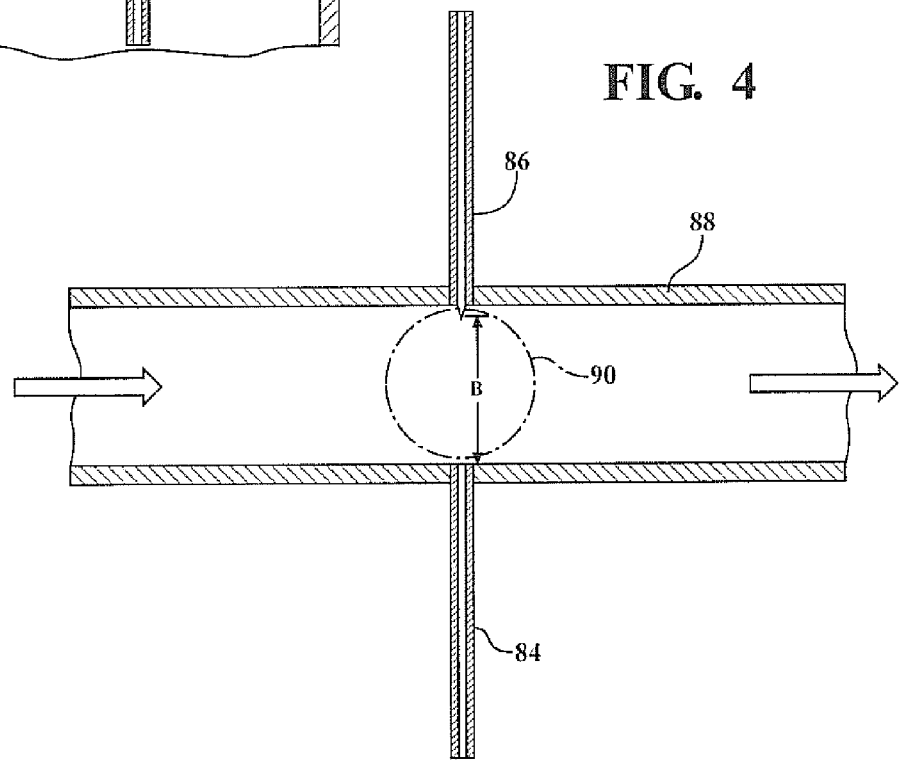
FIG. 4 is a cross sectional view showing part of an alternative embodiment of the present invention.
Figure 5:
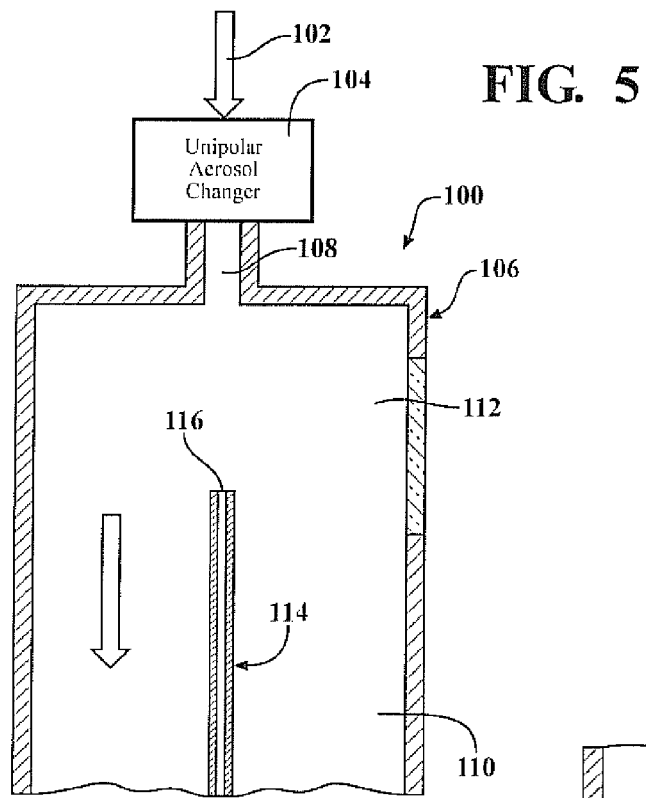
FIG. 5 is a cross sectional view showing part of a further embodiment of the present invention.
Figure 6:
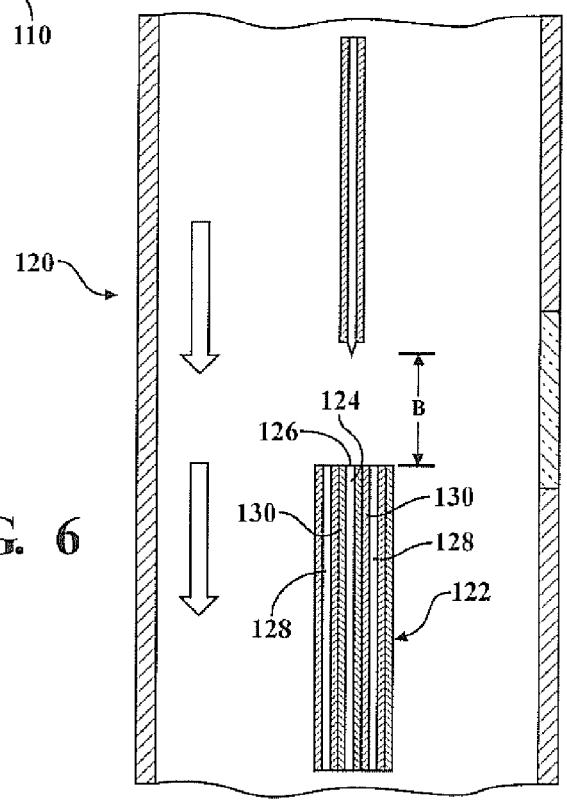
FIG. 6 is a cross sectional view showing a portion of yet another embodiment of the present invention.
Figure 7:
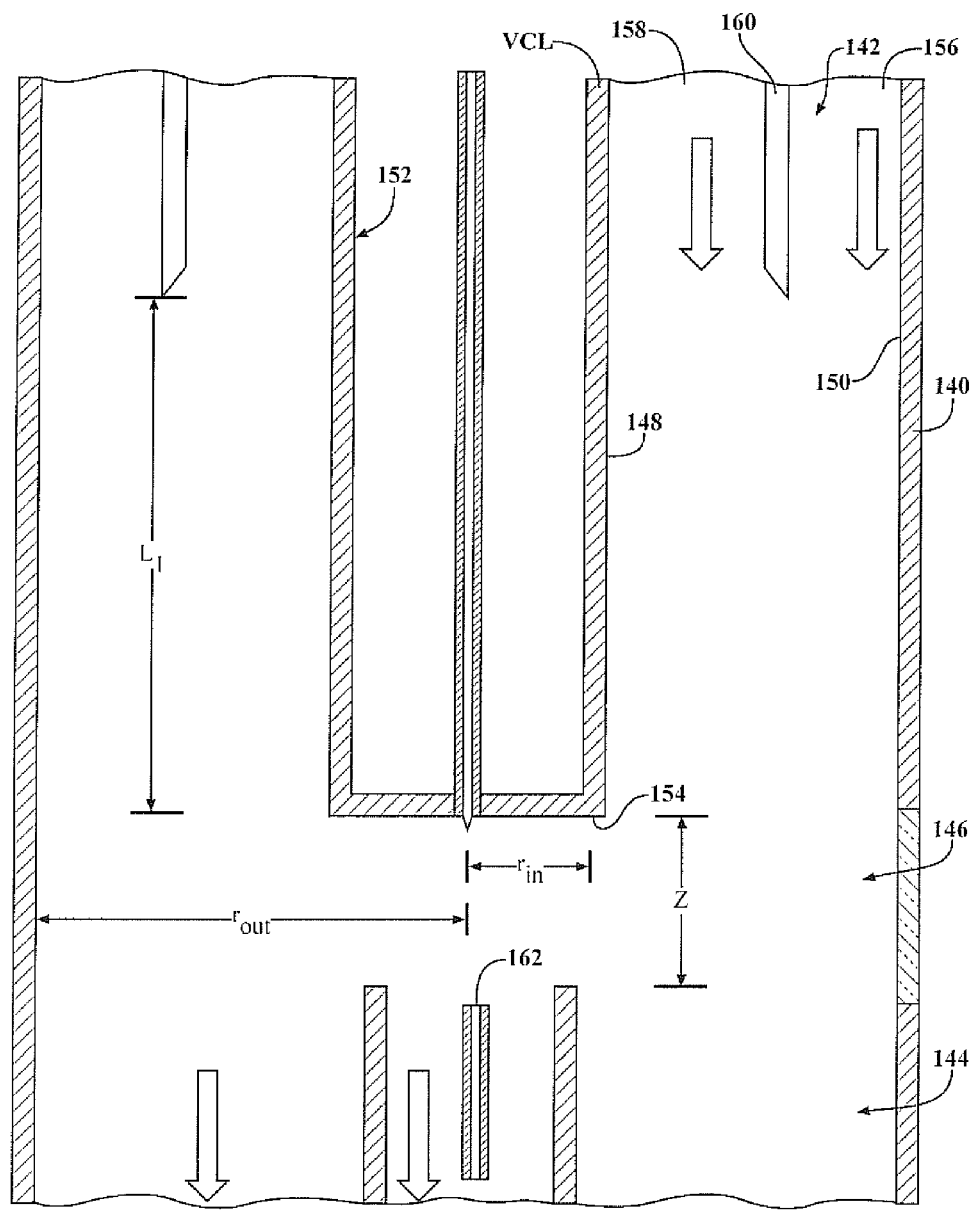
FIG. 7 is a cross sectional view of an embodiment of the present invention utilizing a sheath flow.
Figure 8:
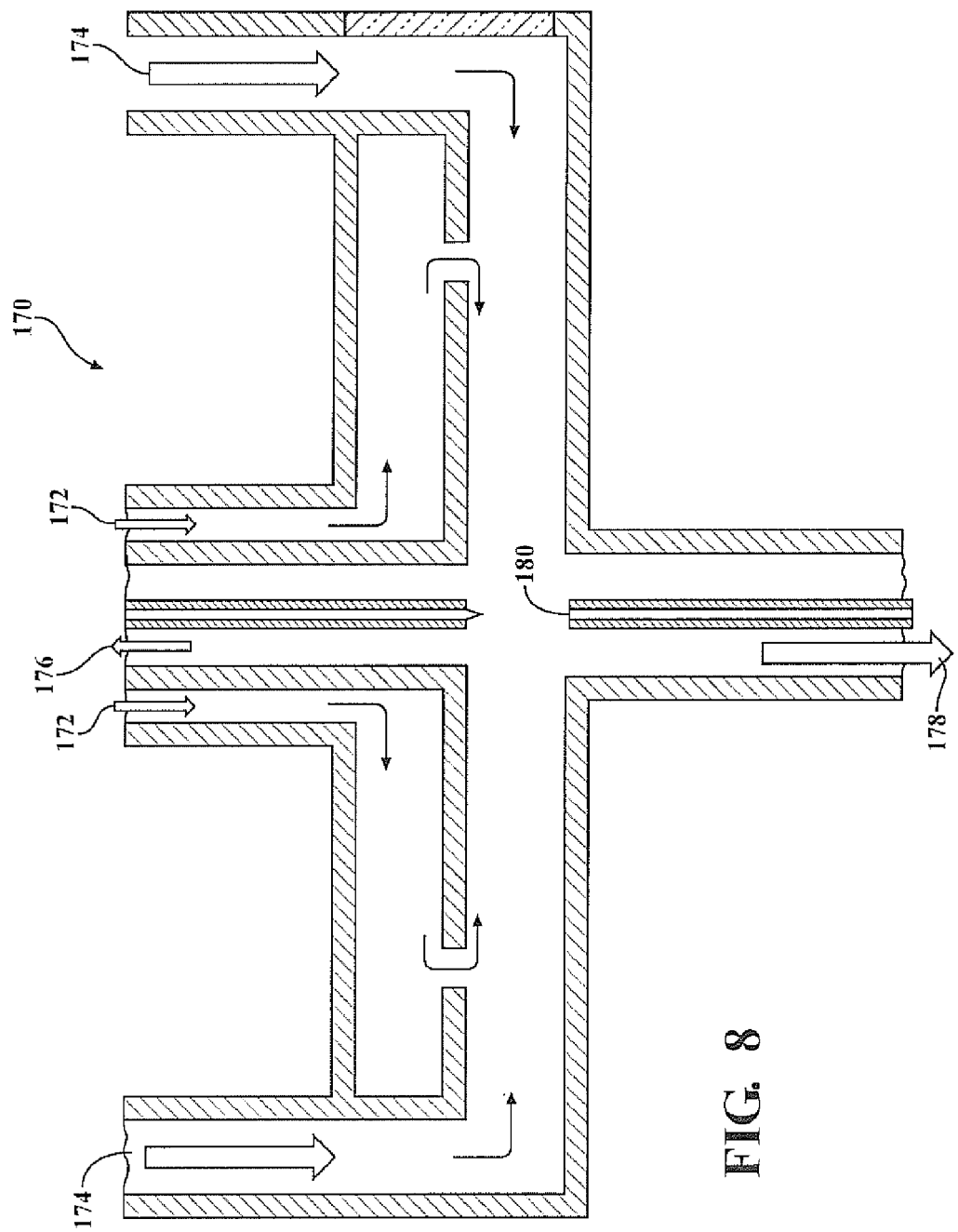
FIG. 8 is a cross sectional view showing a portion of an alternative embodiment of the present invention utilizing a sheath flow.

Referring now to FIG. 3, a further embodiment of the present invention will be described. An apparatus for collection and analysis of particles in aerosol is shown at 58 and includes a housing 60 with an inlet area 62, an outlet area 64, and a collection and analysis area 66. In this embodiment, the housing 60 is generally tubular. In some exemplary embodiments, the tube forming the housing 60 has a diameter which can range from a few millimeters to centimeters. A collection electrode 70 and a second electrode 76 are coaxial with the housing 60 and with one another. They each are insulated with a dielectric layer, 72 and 78 respectively, covering their side surfaces. In one exemplary embodiment, the dielectric sheathing has a thickness in the range of 0.5 to 1 millimeter. The collection electrode 70 has an exposed tip 74. In this embodiment, this tip 74 is flat with the tip surface being generally perpendicular to the axis of the collection electrode 70 and housing 60. The diameter of this tip may vary in size, with some exemplary embodiments having a diameter d in the range of 1 to 1000 microns. In this embodiment, the second electrode 76 has a sharp tip 80 with the tip having a tip radius in the range of 5 to 100 microns. The tips 74 and 80 are spaced apart by a spark gap. The distance of the spark gap in an exemplary embodiment is in the range of 1 to 10 millimeters. An optical window is shown at 82 in a sidewall of the housing 60. A portion of the aerosol flow path is shown at A. As will be clear to those of skill in the art, the aerosol flows along the housing from the inlet area 62, through the collection and analysis area 66, and out through the outlet area 64. As with the prior discussed embodiments, during a collection step, particles of an aerosol flowing along the path A are collected on the tip 74 of the collection electrode 70. In some embodiments, the second electrode 76 is held at a high corona voltage so as to create a cloud of ions for charging of the aerosol flow. During a subsequent step, a spark is generated across the spark gap so as to ablate particles collected on the tip 74. As will be clear to those of skill in the art, such an approach allows a near time analysis, since collection and ablation of particles from the tip may be done sequentially in rapid succession, and repeated as necessary.

FIG. 4 shows an alternative embodiment in which the collection electrode 84 and second electrode 86 extend generally perpendicular to the axis of the housing 88. An optical window is shown at 90 and the spark gap is shown as B.

FIG. 5 shows an alternative embodiment of an apparatus 100 for collection and analysis of particles of an aerosol. An aerosol is introduced at 102 through a unipolar aerosol charger 104, which is operable to charge the particles of the aerosol. The unipolar charger may impart either negative or positive charge to the particles. The housing 106 has an inlet area 108, an outlet area 110, and a collection and analysis area 112. A coaxial collection electrode 114 has a tip 116 in the collection and analysis area 112. In this embodiment, the collection electrode 114 is held at a bias voltage having a polarity opposite to the charge imparted by the unipolar aerosol charger 104. This attracts particles of the aerosol to the tip 116. In this embodiment, at least a portion of the walls of the housing 106 is electrically conductive. This electrically conductive portion forms the complementary second electrode for use during a subsequent step in which a spark is used to ablate particles on the tip 116. During the ablation step, the conductive part of the housing may be held at ground while the collection electrode 114 is energized at a high voltage so as to cause a spark between the tip 116 and the housing 106, thereby ablating particles from the tip 116. The electrically conductive portion of the housing may also be held at ground during the collection step.

Referring now to FIG. 6, a further alternative embodiment of an apparatus 120 will be described. The apparatus 120 differs from the embodiment of FIG. 3 in that the collection electrode is surrounded by concentric assembly of electrodes 122. A central electrode 124 of the electrode assembly 122 serves as a collection electrode. It has a tip 126. A concentric electrode 128 surrounds the central electrode 124 and is separated therefrom by a dielectric layer 130. Additional concentric electrodes, separated by adequate dielectric layers, may be provided, if needed. During the collection step, the central electrode 124 is held at a bias voltage. This may be ground or may be a bias voltage opposite to the potential of the other electrode. In the example in which the central electrode is held at a bias voltage, the concentric electrodes may be held at the same voltage or at lower levels with the same polarity so as to act as an electrostatic lens that focuses particle capture on the central electrode tip 126. Further concentric electrodes may be provided. This arrangement is used to create an electrostatic lens or funnel to improve particle deposition characteristics on the tip 126.

Referring now to FIG. 7, yet another alternative embodiment of an apparatus in accordance with the present invention will be described. The apparatus has a housing 140 with an inlet area 142, an outlet area 144, and a collection and analysis area 146 interconnecting the inlet area with the outlet area. The inlet area 142 may be said to have concentric inner 148 and outer 150 surfaces with the surfaces spaced apart from one another. In the illustrated embodiment, the housing 140 is generally tubular with the surface 150 being an inner surface of the tubular housing and the surface 148 being an outer surface of a central member 152 that extends coaxially along the housing from the inlet area to a downstream end 154 at the collection and analysis area 146. The surface 148 is defined by the outer surface of the central member 152. In this embodiment, an aerosol inlet 156 is defined adjacent the surface 150 and a sheath inlet 158 is defined between the aerosol inlet and the surface 148. In this embodiment, a coaxial flow guide 160 separates the aerosol inlet 156 from the sheath inlet 158. An aerosol flow path is defined from the aerosol inlet 156 through the collection and analysis area 146 and out through the outlet area 144. A sheath flow path is defined from the sheath inlet 158 through the collection and analysis area 146 and out through the outlet area 144. In preferred embodiments, the surfaces 148 and 150 are each electrically conductive. During the collection step, an aerosol flow is introduced at aerosol inlet 156 and a sheath flow is introduced at sheath inlet 158. The surface 150 may be held at ground relative to surface 148, which is held at a classification voltage. The classification voltage, $V_{CL}$ is opposite in polarity to the charge of the particles in the aerosol flow, and is chosen such that these particles are deflected towards the surface 148 such that they cross the sheath flow. This approach allows separation of particles based on their electrical mobility—and hence size, thereby allowing size-resolved particle collection on the collection electrode tip 162. This tip may be held at ground or at a bias voltage for collection of the particles. By choosing the dimensions $L_l$, $r_{in}$, $r_{out}$, and gap Z, along with the classification voltage, bias voltage, and flow rates, particles within a predetermined size range may be collected on the collection electrode tip 162. As will be clear to those of skill in the art, a charged aerosol may have particles in which the charge on the individual particles corresponds to the size of the particle and therefore particles may be sorted by size in this embodiment. Following the collection step, particles collected on the tip 162 may be ablated as discussed in accordance with prior embodiments.

Referring now to FIG. 8, a further embodiment of a collection and analysis apparatus that allows size-resolved particle collection is shown at 170. In this embodiment, aerosol enters at an aerosol inlet 172 as sheath flow enters at sheath inlet 174. The aerosol flow path is diverted concentrically outwardly and then reversed so as to join the sheath flow. This design may be considered parallel disk geometry with axial symmetry. Some of the sheath flow exits through outlet 176 while some of the aerosol flow exits through outlet 178. As with prior embodiments, particles are collected on tip 180 and then ablated for analysis.

Figures 9, 10:
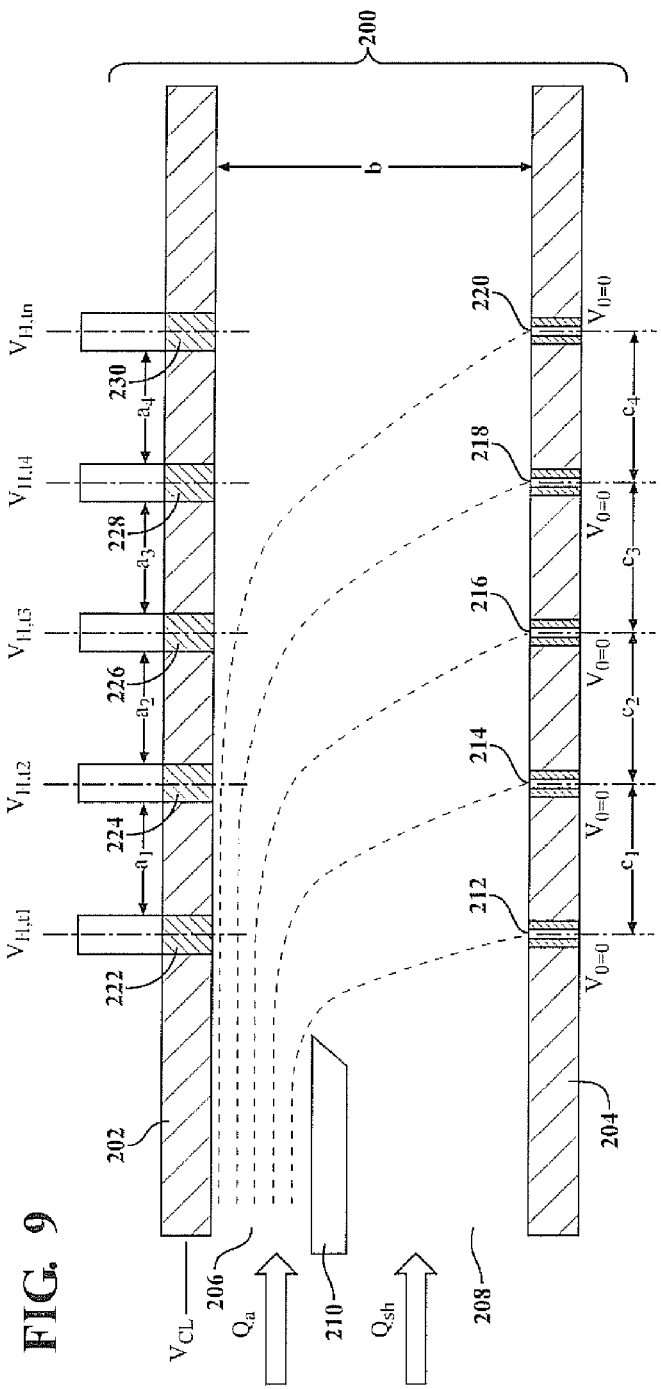
FIG. 9 is a cross sectional view of an embodiment of the present invention utilizing a sheath flow and a plurality of collection electrodes.
FIG. 10 is a top view of a portion of the embodiment of FIG. 9.

Referring now to FIGS. 9 and 10, a further alternative embodiment of an apparatus for collection and analysis of particles of an aerosol will be described. The apparatus is generally shown at 200 in FIG. 9 and has a pair of opposed surfaces 202 and 204. FIG. 10 is a view looking down on surface 204. An aerosol inlet is provided at 206 adjacent the surface 202 as a point source. A sheath inlet is provided at 208 adjacent the surface 204, as a line source. A flow separator is provided at 210 to separate the two inlets. In this embodiment, the collection electrode takes the form of a plurality of collection electrodes 212-220. These collection electrodes have tips that are disposed in or extend from the surface 204 and are insulated therefrom by dielectric layers. The collection electrodes are spaced apart along the surface 204 in the direction of flow. The second electrode takes the form of a plurality of second electrodes 222-230. In this embodiment, the surface 202 is formed of a dielectric material while the surface 204 is formed of metal or another electrically conductive material. The second electrodes 222-230 are spaced apart along the surface 202 in the direction of flow and are positioned in register with the collection electrodes 212-220. This defines a plurality of spark gaps between aligned pairs of electrodes, such as between electrodes 212 and 222. The spark gap has a dimension b. During a collection step, an aerosol flow is introduced through aerosol inlet 206 and a sheath flow is introduced at sheath inlet 208. The aerosol flow is preferably a narrow stream while the sheath flow is a flat and wider flow. The surface 202 is nonconductive, while the surface 204 is held at a classification voltage chosen to cause particles of the aerosol flow to be deflected towards the surface 204. Because particles of different sizes have different charges and masses, these particles will be deflected more or less strongly towards the surface 204. This allows the particles to be sorted by size for collection on the various collection electrode tips 212-220. During a subsequent ablation step, a spark is created between aligned pairs of electrodes so as to ablate the particles on each of the collection electrodes 212-220. Preferably, this is done sequentially such that a spark is first created between electrodes 212 and 222, then a spark is created between electrodes 214 and 224, etc. FIG. 10 shows the tips of the collection electrodes 212-220 and optical windows 232-240 aligned with the various spark gaps.

Figure 11:
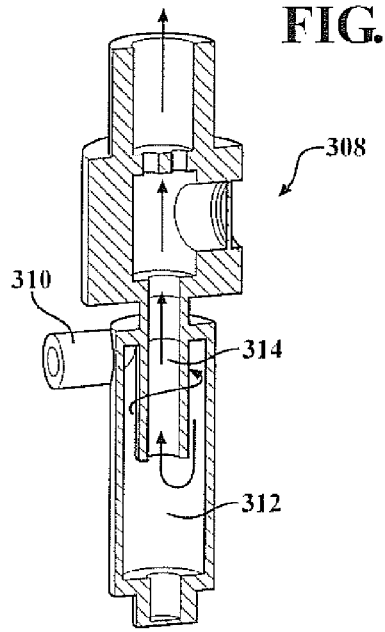
FIG. 11 is a cross sectional perspective view of a portion of yet a further embodiment of the present invention wherein the aerosol flow is sorted by cyclone separators.
Figure 12:
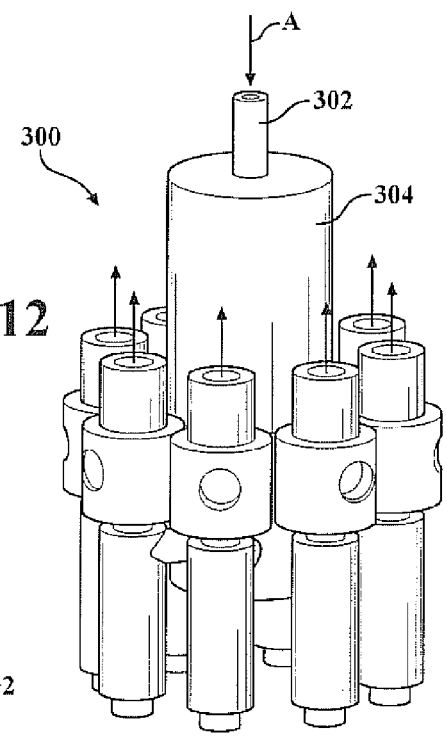
FIG. 12 is a perspective view of an embodiment of the present invention utilizing a plurality of cyclone separators.
Figure 13:
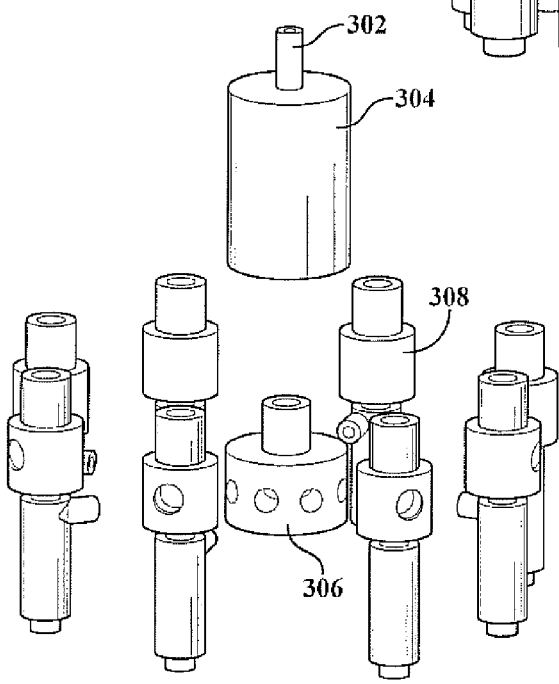
FIG. 13 is an exploded view of the embodiment of FIG. 12.

Referring now to FIGS. 11-13, a further embodiment of the present invention will be discussed. It is desirable to separate the analysis of various types of particles within an aerosol flow. The apparatus 300 shown in FIG. 12 has an aerosol introduced at A through inlet 302 into a charging unit 304. This charging unit may be a unipolar or bipolar charger. The aerosol then flows to a manifold 306, best shown in the exploded view of FIG. 13. The flow is then divided into multiple flows, each of which is introduced to a separator and analysis unit 308. Such a unit 308 is shown in cross section in FIG. 11. The flow enters through inlet 310 and into a cyclone section 312. The cyclone unit 312 is designed such that the flow circulates in a chamber and only particles within a particular size range exit the separator unit 312 through outlet 314. From there, the aerosol flow may be considered to be a sorted aerosol flow and will contain only particles within a certain size or mass range. They are then introduced to a collection and analysis unit as described previously. The plurality of cyclone units 312 may be considered to serve as a size classification unit for separating the flow of aerosol into a plurality of sorted aerosol flows. This approach allows multiplexing of the aerosol collection and analysis method. This allows simultaneous collection of different size fractions of the aerosols, which can be subsequently analyzed instantaneously. This considerably reduces measurement time, and improves the time resolution of size-resolved measurements. The multiplexing can also be done with respect to other aerosol properties, such as humidity or temperature to name a few.

In some embodiments, analysis of particles may be conducted at different temperatures, such as by heating the collection tip to different temperatures to study how spectroscopic signal changes as a function of temperature. As will be clear to those of skill in the art, this temperature change may have many applications.

As will be clear to those of skill in the art, the herein described embodiments of the present invention may be altered in various ways without departing from the scope or teaching of the present invention. It is the following claims, including all equivalents, which define the scope of the present invention.

The invention claimed is:

1. A method for collecting and analyzing particles of a flow of aerosol, the method comprising:

providing a housing having an inlet area and an outlet area, the housing further having a collection and analysis area interconnecting the inlet area with the outlet area, a flow path for an aerosol being defined from the inlet area, through the collection and analysis area, and out the outlet area;

providing a collection electrode having a tip disposed in the flow path in the collection and analysis area;

providing a second electrode spaced from the collection electrode tip so as to define a spark gap in the collection an analysis area;

providing a corona current between the second electrode and the collection electrode such that a cloud of ions is created between the electrodes, the particles of the aerosol being charged by the ions from the second electrode;

introducing a flow of aerosol along the flow path;

collecting particles of the aerosol on the tip of the collection electrode;

applying a high voltage spark across the spark gap so as to ablate the particles collected on the tip of the collection electrode thereby creating atomic emissions;

providing an optical window defined in the housing, the window being aligned with the spark gap; and collecting atomic emissions produced during at least part of the spark step for analysis of the ablated particles.

2. A method for collecting and analyzing particles of a flow of aerosol in accordance with claim 1, wherein:

the particles of the aerosol passing along the flow path are charged; and the collection step further comprising holding the collection electrode at a bias voltage relative to the charged particles such that charged particles collect on the tip of the electrode.

3. A method for collecting and analyzing particles of a flow of aerosol in accordance with claim 2, wherein:

during the collection step, holding the second electrode at a second voltage relative to the bias voltage so as to create an electrical field urging charged aerosol particles toward the tip of the collection electrode.

4. A method for collecting and analyzing particles of a flow of aerosol in accordance with claim 2, further comprising:

providing a collection electrode assembly, wherein the collection electrode comprises a central electrode of the collection electrode assembly, the assembly further including at least one concentric electrode surrounding the central electrode and a dielectric layer separating the central electrode from the concentric electrode, the concentric electrode being held at a potential greater than the central electrode when the central electrode is held at the bias voltage relative to the charged particles.

5. A method for collecting and analyzing particles of a flow of aerosol in accordance with claim 2, wherein:
the inlet area of the housing has a first surface and a second surface spaced therefrom, the first and second surfaces each formed of an electrically conductive material, an aerosol inlet defined adjacent the first surface and a sheath flow inlet defined between the aerosol inlet and the second surface of the inlet area;
the flow path for an aerosol defined from the aerosol inlet of the inlet area, through the collection and analysis area, and out the outlet area;
a sheath flow path being defined from the sheath inlet of the inlet area, through the collection and analysis area, and out the outlet area;
during the collection step the first surface of the inlet area being grounded relative to the charged particles, a sheath flow being introduced along the sheath flow path, and the second surface being held at a classification voltage chosen such that a portion of the charged particles are deflected toward the second surface and towards the collection electrode tip.

6. A method for collecting and analyzing particles of a flow of aerosol in accordance with claim 5, wherein:
the housing comprises an elongated tube defining at least the inlet area and the collection and analysis area, the first surface of the inlet area being defined by an inner surface of the tube; and
further comprising providing a central member extending axially along the inlet area of the housing to a downstream end, the central member having an outer surface defining the second surface of the inlet area.

7. A method for collecting and analyzing particles of a flow of aerosol in accordance with claim 6, further comprising:
providing a coaxial flow guide disposed in the inlet area between the central member and the elongated tube, the coaxial flow guide having a downstream end disposed upstream of the downstream end of the central member;
the aerosol flow path extending between the flow guide and the elongated tube and the sheath flow path extending between the flow guide and the central member.

8. A method for collecting and analyzing particles of a flow of aerosol in accordance with claim 6, wherein:
the second electrode has a tip adjacent the downstream end of the central member.

9. A method for collecting and analyzing particles of a flow of aerosol in accordance with claim 2, wherein:
the housing has a first surface and an opposed second surface, the first surface formed of an electrically conductive material, the second surface formed of a dielectric material;
an aerosol inlet being defined adjacent the first surface in the inlet area of the housing, the flow path for an aerosol defined from the aerosol inlet of the inlet area, through the collection and analysis area, and out the outlet area;
a sheath flow inlet being defined between the aerosol inlet and the second surface, a sheath flow path being defined from the sheath flow inlet, through the collection and analysis area, and out through the outlet area;
wherein the collection electrode comprises providing a plurality of collection electrodes having tips disposed in or extending from the second surface, the tips of the plurality of collection electrodes being spaced apart along the second surface in tile collection and analysis area;
wherein the second electrode comprises providing a plurality of second electrodes disposed in or extending from the first surface, the plurality of second electrodes being spaced apart along the first surface in register with the collection electrodes so as to define a plurality of spark gaps; and
wherein the providing a corona current comprises providing a corona current between at least one of the second electrodes and one of the collection electrodes;
during the collection step;
the plurality of electrodes each being held at a bias voltage relative to the charged particles;
a sheath flow being introduced along the sheath flow path; mad the first surface being held at a classification voltage such that a portion of the charged particles are deflected toward the second surface for collection on the tips of the plurality of spaced apart electrodes; and
wherein each electrode tip collects particles of a different charge; and
during the spark applying step;
applying a high voltage spark across each of the plurality of spark gaps.

10. A method for collecting and analyzing particles of a flow of aerosol in accordance with claim 9, wherein:
during the spark applying step, a high voltage spark is applied across each spark gap at a different time.

11. A method for collecting and analyzing particles of a flow of aerosol in accordance with claim 9, further comprising:
a flow guide disposed in the inlet area between the aerosol flow path and the sheath flow path.

12. A method for collecting and analyzing particles of a flow of aerosol in accordance with claim 1, wherein:
the second electrode and collection electrode are each elongated and are coaxial with one another.

13. A method for collecting and analyzing particles of a flow of aerosol in accordance with claim 12, wherein:
the housing is elongated and the second electrode and collection electrode extend coaxially along the housing, the window being disposed in a side wall of the housing.

14. A method for collecting and analyzing particles of a flow of aerosol in accordance with claim 1, further comprising:
providing a charger for charging particles of the flow of aerosol;
providing a size classification unit operable to sort particles of the flow of aerosol into a plurality of sorted aerosol flows, each sorted flow having particles within a predetermined size range;
the collection electrode and the second electrode being part of a plurality of collection electrodes and second electrodes each separated so as to define a spark gap, each collection electrode being disposed in a flow path for one of the sorted flows.

15. A method for collecting and analyzing particles of a flow of aerosol in accordance with claim 14, wherein:
the size classification unit comprises a plurality of cyclone separators.

16. A method for collecting and analyzing particles of a flow of aerosol in accordance with claim 1, further comprising:
providing a broadband optical spectrometer in optical communication with the optical window; and
analyzing the atomic emissions using the spectrometer.

17. A method for collecting and analyzing particles of a flow of aerosol in accordance with claim 16, further comprising:
  providing a fiber optic cable, an end of the fiber optic cable forming or being in optical communication with the optical window, and an opposite end of the fiber optic cable being in optical communication with the spectrometer.

18. A method for collecting and analyzing particles of a flow of aerosol in accordance with claim 1, further comprising:
  providing a laser light source;
  using the laser light source to ablate particles on the collection electrode tip prior to applying the high voltage spark.

19. A spark emission spectroscopy device for collecting and analyzing particles of a flow of aerosol, the spectroscopy device comprising:
  a housing having an inlet area and an outlet area, the housing further having a collection and analysis area interconnecting the inlet area with the outlet area, a flow path for an aerosol being defined from the inlet area, through the collection and analysis area, and out the outlet area;
  a collection electrode having a tip disposed in the collection and analysis area and in the flow path for collection of particles of an aerosol thereon;
  a second electrode spaced from the collection electrode tip so as to define a spark gap in the collection and analysis area, wherein a corona current is produced between the second electrode and the collection electrode such that a cloud of ions is created between the electrodes;
  an optical window defined in the housing, the window being aligned with the spark gap;
  a high voltage pulse generator connected to the collection electrode and second electrode for generation of a spark across the spark gap;
  wherein the collection electrode is held at a bias voltage during a collection step, whereby charged particles of a flow of aerosol passing along the flow path are collected on the collection electrode tip; and
  wherein during a spark ablation step a high voltage pulse is applied between the second electrode and collection electrode tip so as to create a spark across the spark gap, thereby ablating aerosol particles collected on the tip of the collection electrode.

20. A method of collecting and analyzing particles of a flow of aerosol, the method comprising:
  providing a housing having an inlet area and an outlet area, the housing further having a collection and analysis area interconnecting the inlet area with the outlet area;
  the inlet area of the housing having a first surface and a second surface spaced therefrom, an aerosol inlet defined adjacent the first surface and a sheath flow inlet defined between the aerosol inlet and the second surface of the inlet area;
  a flow path for an aerosol defined from the aerosol inlet of the inlet area, through the collection and analysis area, and out the outlet area;
  a sheath flow path being defined from the sheath inlet of the inlet area, through the collection and analysis area, and out the outlet area;
  providing a collection electrode having a tip disposed in the aerosol flow path in the collection and analysis area;
  providing a second electrode spaced from the collection electrode tip so as to define a spark gap in the collection and analysis area;
  during a collection step
  introducing a flow of aerosol along the aerosol flow path, the particles of the aerosol being charged; and providing a corona current between the second electrode and the collection electrode such that a cloud of ions is created between the electrodes;
  introducing a sheath flow along the sheath flow path;
  holding the collection electrode at a bias voltage relative to the charged particles;
  holding one of the first or second surfaces of the inlet area at a classification voltage chosen such that a portion of the charged particles are deflected toward the tip of the collection electrode; and
  ablating the particles collected on the tip of the collection electrode, thereby creating atomic emissions; and
  collecting atomic emissions produced during at least part of the spark step for analysis of the ablated particles.

21. A method for collecting and analyzing particles of a flow of aerosol in accordance with claim 20, further comprising:
  providing a second electrode spaced from the collection electrode tip so as to define a spark gap in the collection and analysis area;
  providing a high voltage pulse generator connected to the collection electrode and second electrode for generation of a spark across the spark gap; and
  applying a high voltage spark across the spark gap so as to perform the ablating step.

22. A method for collecting and analyzing particles of a flow of aerosol in accordance with claim 20, wherein:
  the first and second surfaces each are formed of an electrically conductive material;
  during the collection step the first surface of the inlet area being grounded relative to the charged particles; and
  the second surface being the surface held at the classification voltage chosen such that a portion of the charged particles are deflected towards the second surface and towards the tip of the collection electrode.

23. A method for collecting and analyzing particles of a flow of aerosol in accordance with claim 20, wherein:
  the first surface of the inlet area being formed of an electrically conductive material, the second surface of the inlet area being formed of a dielectric material;
  the collection electrode comprising a plurality of collection electrodes having tips disposed in or extending from the second surface, the tips of the plurality of collection electrodes being spaced apart along the second surface in the collection and analysis area;
  during the collection step:
    the plurality of collection electrodes each being held at a bias voltage relative to the charged particles; and
    the first surface being the surface held at the classification voltage such that a portion of the charged particles are deflected towards the second surface for collection on the tips of the plurality of spaced apart collection electrodes;
  wherein each collection electrode tip collects particles of a different charge; and
  during the ablating step, ablating the particles collected on the tips of each of the collection electrodes.

* * * * *

UNITED STATES PATENT AND TRADEMARK OFFICE
CERTIFICATE OF CORRECTION

Page 1 of 1

PATENT NO. : 8,970,840 B2
APPLICATION NO. : 13/315372
DATED : March 3, 2015
INVENTOR(S) : Pramod Kulkarni et al.

It is certified that error appears in the above-identified patent and that said Letters Patent is hereby corrected as shown below:

In the Claims

Column 10, line 33: Replace "an" with --and--; and
Column 12, line 17: Replace "mad" with --and--.

Signed and Sealed this
Fourth Day of August, 2015

Michelle K. Lee
*Director of the United States Patent and Trademark Office*